(12) United States Patent
Stephens

(10) Patent No.: US 10,888,708 B2
(45) Date of Patent: Jan. 12, 2021

(54) PHOTOTHERAPY DEVICE WITH REAL-TIME MORPHOLOGIC FEEDBACK AND GUIDANCE

(71) Applicant: QC, LLC, Franklin, TN (US)

(72) Inventor: Bryan James Stephens, Franklin, TN (US)

(73) Assignee: QC, LLC, Franklin, TN (US)

( * ) Notice: Subject to any disclaimer, the term of this patent is extended or adjusted under 35 U.S.C. 154(b) by 778 days.

(21) Appl. No.: 15/349,763

(22) Filed: Nov. 11, 2016

(65) Prior Publication Data

US 2017/0128740 A1 May 11, 2017

Related U.S. Application Data

(60) Provisional application No. 62/253,916, filed on Nov. 11, 2015.

(51) Int. Cl.
| *A61N 5/06* | (2006.01) |
| *A61N 5/00* | (2006.01) |
| *A61B 17/00* | (2006.01) |
| *A61B 18/00* | (2006.01) |

(52) U.S. Cl.
CPC ......... *A61N 5/0613* (2013.01); *A61N 5/0616* (2013.01); *A61B 2017/00057* (2013.01); *A61B 2017/00106* (2013.01); *A61B 2018/00648* (2013.01); *A61B 2018/00791* (2013.01); *A61N 2005/005* (2013.01); *A61N 2005/063* (2013.01); *A61N 2005/0626* (2013.01); *A61N 2005/0644* (2013.01); *A61N 2005/0659* (2013.01); *A61N 2005/0662* (2013.01)

(58) Field of Classification Search
CPC ................ A61N 5/0616; A61N 5/0624; A61N 2005/0628; A61N 2005/0626; A61N 2005/0644; A61N 2005/063; A61N 5/0613; A61N 2005/005; A61N 2005/0659; A61N 2005/0662; A61B 2018/00648; A61B 2017/00057; A61B 2017/00106; A61B 2018/00791
See application file for complete search history.

(56) References Cited

U.S. PATENT DOCUMENTS

| 6,210,425 B1 | 4/2001 | Chen |
| 6,238,426 B1 | 5/2001 | Chen |
| 7,171,253 B2 | 1/2007 | Dowlatshahi |
| 7,355,155 B2 | 4/2008 | Wang |
| 7,366,214 B2 | 4/2008 | Liu et al. |
| 8,518,094 B2 | 8/2013 | Wang |
| 2005/0177093 A1 | 8/2005 | Barry et al. |
| 2007/0195548 A1 | 8/2007 | Wang |
| 2007/0239146 A1 | 10/2007 | Wang |

(Continued)

FOREIGN PATENT DOCUMENTS

| WO | WO 2015/200380 A1 | 12/2015 |
| WO | WO 2018/026680 A1 | 2/2018 |

*Primary Examiner* — Tammie K Marlen
(74) *Attorney, Agent, or Firm* — Williams Mullen; Andrew R. Shores; Douglas C. Tsao

(57) ABSTRACT

A phototherapy device for promoting wound healing and treating pain associated with soft-tissue and musculo-skeletal injuries is presented. The phototherapy device may deliver therapeutic light outputs that are variable, in real time, based in part on morphologic data of the patient measured by the device in real-time.

16 Claims, 9 Drawing Sheets

(56) References Cited

U.S. PATENT DOCUMENTS

| | | |
|---|---|---|
| 2008/0033412 A1 | 2/2008 | Whelan et al. |
| 2008/0091249 A1 | 4/2008 | Wang |
| 2008/0195087 A1 | 8/2008 | Wang et al. |
| 2008/0255638 A1 | 10/2008 | Wang |
| 2008/0262394 A1 | 10/2008 | Pryor et al. |
| 2008/0306472 A1 | 12/2008 | Pryor et al. |
| 2009/0012587 A1 | 1/2009 | Wang et al. |
| 2009/0082759 A1 | 3/2009 | Pryor et al. |
| 2009/0153837 A1 | 6/2009 | Wang et al. |
| 2009/0254155 A1 | 10/2009 | Karnarsky et al. |
| 2009/0299236 A1 | 12/2009 | Pryor et al. |
| 2010/0241038 A1 | 9/2010 | Sullivan et al. |
| 2010/0256541 A1 | 10/2010 | Pryor et al. |
| 2010/0286576 A1 | 11/2010 | Pryor et al. |
| 2011/0009852 A1 | 1/2011 | Pryor et al. |
| 2011/0020173 A1 | 1/2011 | Pryor et al. |
| 2011/0144724 A1 | 6/2011 | Pryor et al. |
| 2011/0144725 A1 | 6/2011 | Pryor et al. |
| 2011/0144726 A1 | 6/2011 | Pryor et al. |
| 2011/0224584 A1 | 9/2011 | Pryor et al. |
| 2012/0095533 A1 | 4/2012 | Wang |
| 2012/0303100 A1 | 11/2012 | Pryor et al. |
| 2013/0304164 A1 | 11/2013 | Zanata et al. |
| 2014/0303608 A1* | 10/2014 | Taghizadeh ............ A61B 18/18 606/20 |
| 2015/0182758 A1* | 7/2015 | Ajiki .................... A61N 5/0616 607/88 |
| 2016/0184016 A1 | 6/2016 | Albright |
| 2016/0192988 A1 | 7/2016 | Albright |
| 2016/0256706 A1 | 9/2016 | Harrison |
| 2016/0279436 A1 | 9/2016 | Wang et al. |
| 2017/0128736 A1 | 5/2017 | Johnson et al. |

* cited by examiner

PHOTOTHERAPY DEVICE WITH REAL-TIME MORPHOLOGIC FEEDBACK AND GUIDANCE

CROSS REFERENCE TO RELATED APPLICATIONS

This application claims priority to U.S. Provisional Application No. 62/253,916, filed Nov. 11, 2015, the entirety of which is incorporated herein by reference.

FIELD

The present disclosure generally relates to a phototherapy device. More particularly, the presently disclosed subject matter is directed to a phototherapy device that obtains real-time information about the morphology of a patient and uses that real-time information to adjust the device's output parameters in real-time with little or no user intervention.

BACKGROUND

The present disclosure pertains generally to phototherapy devices. Phototherapy has been shown to promote wound healing and treat pain associated with soft-tissue and musculo-skeletal injuries. Many conventional phototherapy devices use pre-developed treatment protocols (i.e. dose prescriptions, treatment times, power and frequency settings, etc.) to guide users in the treatment of patients. In some cases, these protocols take the form of a booklet or treatment atlas, while in others they are programmed into the graphical user interface (GUI) built into the software of the device. In either case, a user is required to estimate or otherwise make assumptions about certain information regarding the patient to be treated (e.g., skin/coat color, anatomy to be treated, weight of patient, chronicity of ailment, diagnosis of condition, etc.). These estimations are then used as inputs in a lookup table structure (whether in the treatment atlas or in the software GUI). From these input estimates, the user is guided to program a laser (either manually or automatically) with what the manufacturer believes to be the most appropriate treatment protocol for a given patient and his/her/its condition. The patient may be any human or animal, or any other species that may benefit from treatments provided by the device disclosed herein. These protocols are intended to assure some level of certainty about the surface area to treated, subcutaneous depth of structures that can be affected, and efficacy of the overall treatment, based on a combination of ideas from similar (or legacy) products, published literature, and/or opinions of experts or existing clientele.

This conventional approach is fundamentally flawed because, among other things, it relies on a user-based estimation of the condition to be treated. The truly essential factors that dictate both light penetration and overall efficacy of treatment (e.g., tissue composition, depth of relevant structures, the color of skin/hair traversed over the actual area treated, etc.), are not measured but simply estimated (and often very crudely). Merely estimating these important characteristics through a combination of a few broadly defined inputs (e.g. shoulder of light-skinned patient that weighs 120 lbs.) results in less effective treatment. The present invention is designed to overcome these and other shortcomings and measure important characteristics directly, in real-time, and use their values to determine/modify (also in real-time) the parameters of the delivered therapy.

SUMMARY

In some embodiments, a phototherapy device is provided that may include a central processing unit; a therapeutic light source and output; an ultrasound generator and transducer; and a light sensor; wherein the therapeutic light source comprises a plurality of light sources of varying wavelengths and variable intensity; and further wherein the central processing unit controls the intensity and wavelengths of light generated and provided to the output based on one or more user inputs, received ultrasound signals, and light sensor inputs provided to the central processing unit. In some embodiments, the central processing unit may include one or more separate central processing units, and the one or more central processing units may be housed in one or more separate housings.

In some embodiments, light therapy may be provided to a patient by first providing a phototherapy device according to the present disclosure. A user may then input certain treatment parameters and patient information into the phototherapy device. The device may then begin to output therapeutic light for treating the patient, while at the same time measuring morphologic properties of the patient being treated, and adjusting in real-time the output characteristics of the therapeutic light based on those measured morphologic properties of the patient.

DETAILED DESCRIPTION

The presently disclosed subject matter now will be described more fully hereinafter with reference to the accompanying drawings in which some, but not all, embodiments of the presently disclosed subject matter are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated drawings. Therefore, it is to be understood that the presently disclosed subject matter is not to be limited to the specific embodiments disclosed and that modifications and other embodiments are intended to be included within the scope of the appended claims.

In some embodiments, the presently disclosed subject matter provides a phototherapy device. In some embodiments, the disclosed phototherapy device may generally include a controllable therapeutic light source; one or more sensors for determining, in real-time, morphologic properties of the patient being treated; and a central processing unit capable of adjusting, in real-time, output characteristics of the therapeutic light being provided to the patient based on the morphologic properties of the patient measured in real-time by the one or more sensors. The phototherapy device may further include a necessary power supply component(s), light driver(s), and cooling mechanism(s) to ensure proper operation of the device. In some embodiments, the device may also include one or more display screens and/or user inputs for displaying information to and/or receiving information from a user of the device. Further still, those having skill in the art will appreciate that the device may optionally be divided into two or more components (e.g., a central control unit and a therapy head) that may be coupled together using, for example, a cable or wireless transmitter.

Figure 1:
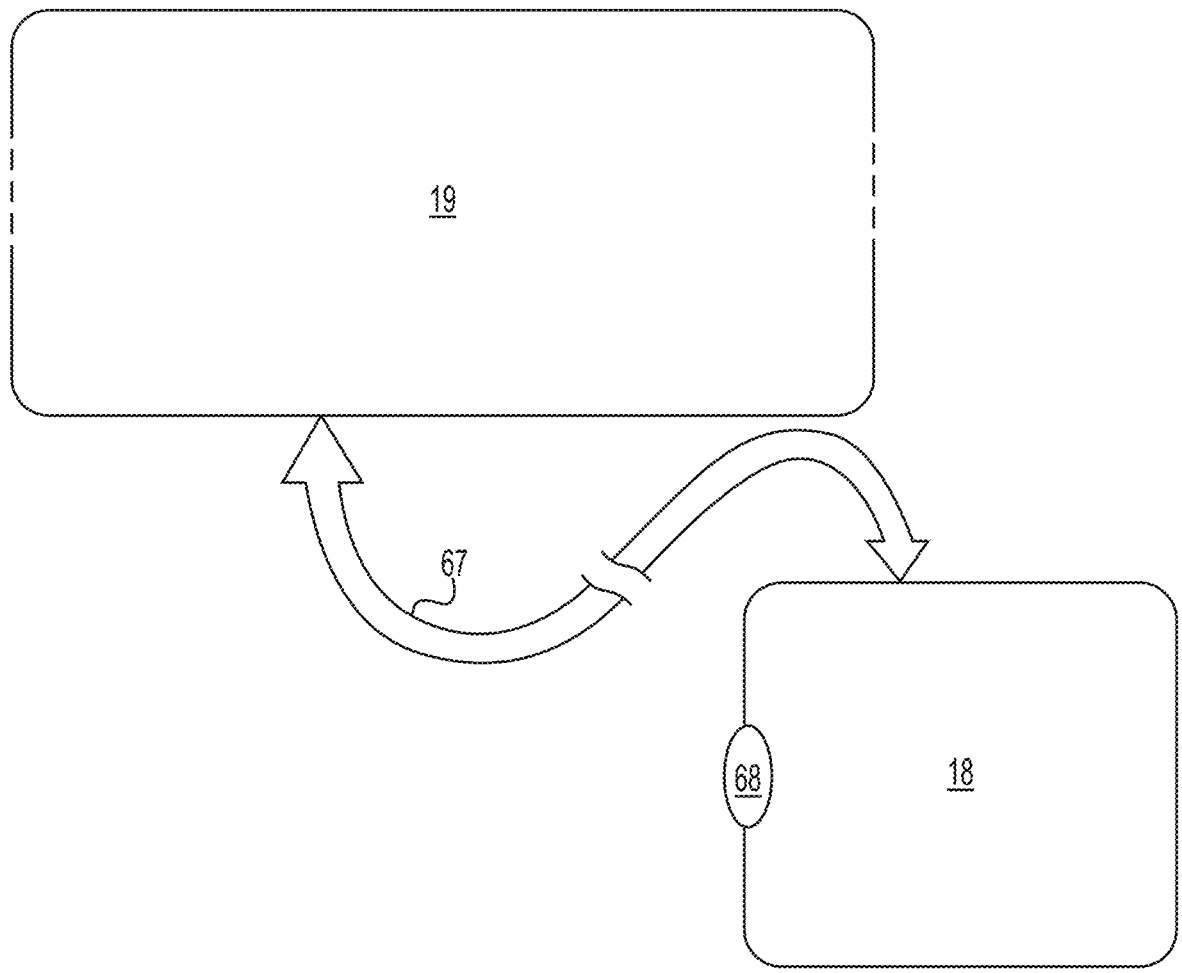
FIG. 1 is a schematic diagram of the disclosed phototherapy device according to one embodiment.

Referring now to FIG. 1, one exemplary embodiment of the presently disclosed phototherapy device is presented that may include a central control unit 19 and a therapy head 18. The central control unit 19 may be connected to therapy head 18 by way of, for example, a shielded cable 67. Therapy head 18 may also include finger switch 68.

Figure 2:
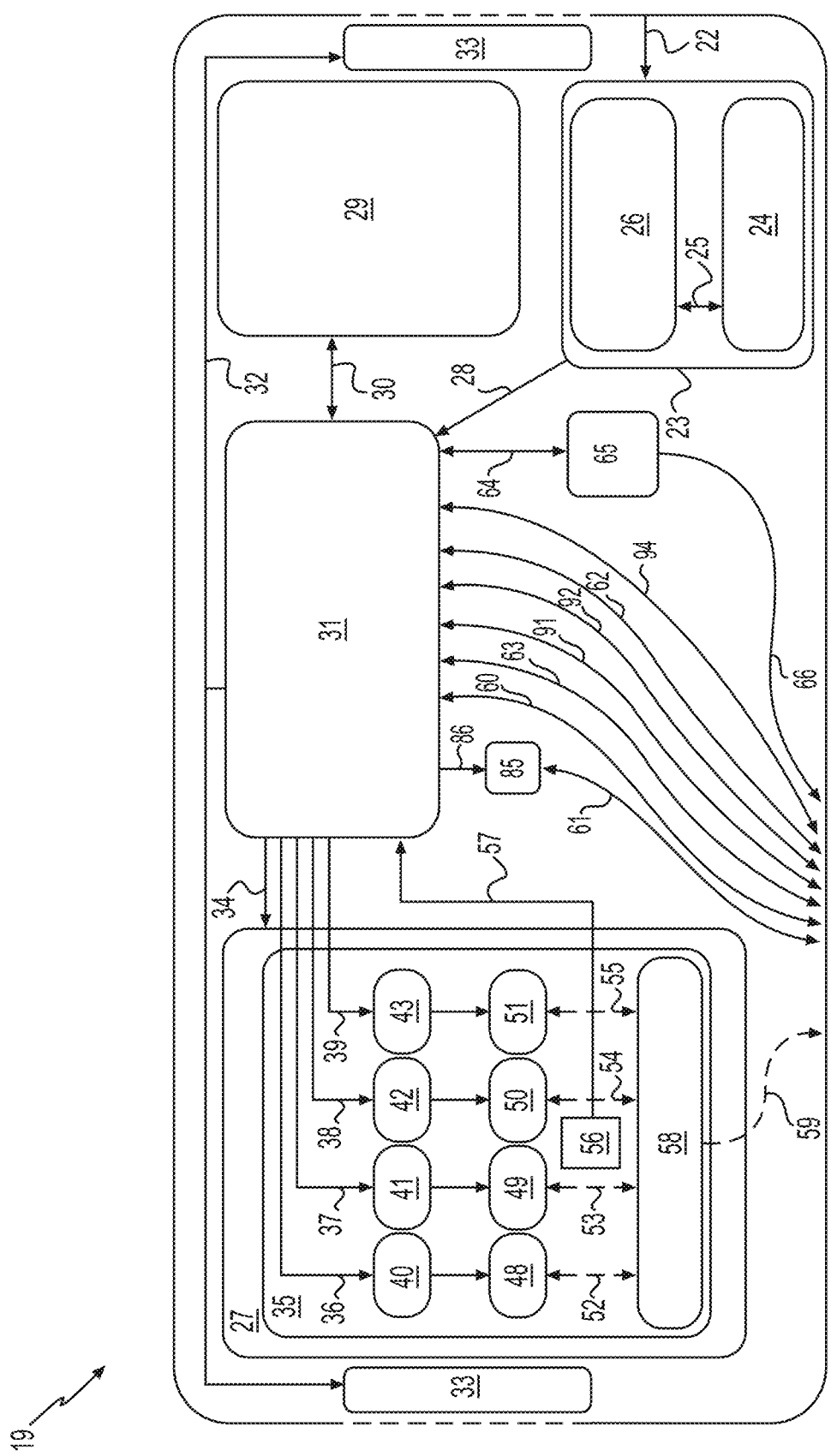
FIG. 2 is a schematic diagram of a central control unit of the disclosed phototherapy device according to one embodiment.

Referring now to FIG. 2, a more detailed view of central control unit 19 according to some embodiments is presented illustrating additional components that may be included. In some embodiments, the central control unit 19 may include a power supply 23; a central processing unit (CPU) 31; an ultrasound generator 65; a display screen and/or user input mechanism (e.g. a touchscreen 29); one or more light sources (e.g. light sources 48, 49, 50, 51), corresponding light source drivers (e.g. light source drivers 40, 41, 42, 43), and corresponding fiber optic waveguides 52, 53, 54, 55; optic coupler 58; a thermo-electric cooler 35; and one or more ventilation fans 33.

Power supply 23 may receive electricity from, for example, leads 22 that may be coupled to an external power source (e.g., a standard 110V power outlet). The central control unit 19 may also be configured to operate using power provided by a battery 24 which may connect to power conversion circuitry 26 via leads 25. For simplicity of illustration, the power supply 23 shown in FIG. 2 supplies power to a central processing unit (CPU) 31 via leads 28, which may, in turn, power other components. In some embodiments, individual components may optionally be connected directly to power supply 23.

CPU 31 may be coupled to other components within the central control unit 19 using various types of connections, including for example: one-way outgoing control, one-way incoming signals, and two-way feedback connections. Arrows on lines in FIG. 2 indicate the direction of power, signal, and/or light in an exemplary embodiment. For example, CPU 31 may have outgoing control connections to ultrasound generator 65 by way of leads 64, thermo-electric cooler 35 by way of leads 34, ventilation fans 33 by way of leads 32, driver 85 of electrically tuned optic lens 76 (FIG. 3) by way of leads 86, a plurality of light source drivers 40, 41, 42, 43 by way of leads 36, 37, 38, 39, and/or electronic display 93 (FIG. 3) by way of leads 94. Further, CPU 31 may have one-way incoming signal connections from power supply 23 by way of leads 28, temperature sensor 56 by way of leads 57, finger switch 68 by way of leads 60, ultrasound receiver 72 (FIG. 3) by way of leads 62, and/or camera 89 (FIG. 3) by way of leads 91. Further still, CPU 31 may include two-way feedback connections to the touch screen 29 by way of leads 30 (including, in some embodiments, a separate graphics card), Red-Green-Blue (RGB) fiber-optic sensor 70 (FIG. 3) by way of leads 63, and/or proximity sensor 90 (FIG. 3) by way of leads 92.

Ultrasound generator 65 may, in some embodiments, deliver a signal to ultrasound transmitter 73 (FIG. 3) by way of leads 66 under command of CPU 31 by way of leads 64. In certain other embodiments, ultrasound generator 65 may be integrated into ultrasound transducer 71 (FIG. 3), resulting in a ultrasound component. Regardless of how implemented, ultrasound generator 65 and transducer 71 (FIG. 3) may be used to determine whether the device is or is not in contact with the patient (which can affect the type of light therapy provided and therefore the therapeutic light needed) and/or provide information to the device about morphologic properties of the patient at and below skin level.

The plurality of independent light source drivers 40, 41, 42, 43 may each connect to and control its own light sources 48, 49, 50, 51. The output light from each light source 48, 49, 50, 51 may range, for example, in wavelength from 400-1,100 nm (or a broader range if desired), which is a wavelength range of light that has been shown to promote wound healing and treat pain associated with soft-tissue and musculo-skeletal injuries. These light sources may each generate and deliver therapeutic light to an optic coupler 58 via, for example, fiber optic waveguides 52, 53, 54, 55. At optic coupler 58, the light rays from each light source may be joined into one output fiber optic waveguide 59. Fiber optic waveguide 59 may then carry the light to output 69 (FIG. 3) where the light may be passed through a lens to ensure proper beam formation.

The light drivers 40, 41, 42, 43 and light sources 48, 49, 50, 51 may generate excess heat during operation. To control the overall temperature of the device and/or its internal components, a cooling mechanism may be employed that may be controlled by, for example, the CPU 31. In some embodiments, a thermo-electric cooler 35 may be employed which may, in turn, be thermally coupled to heat sink 27. The extent to which the thermo-electric cooler 35 is regulated may, in some embodiments, be influenced by temperature sensor 56 whose readings may be relayed to CPU 31 by way of electrical leads 57.

Figure 3:
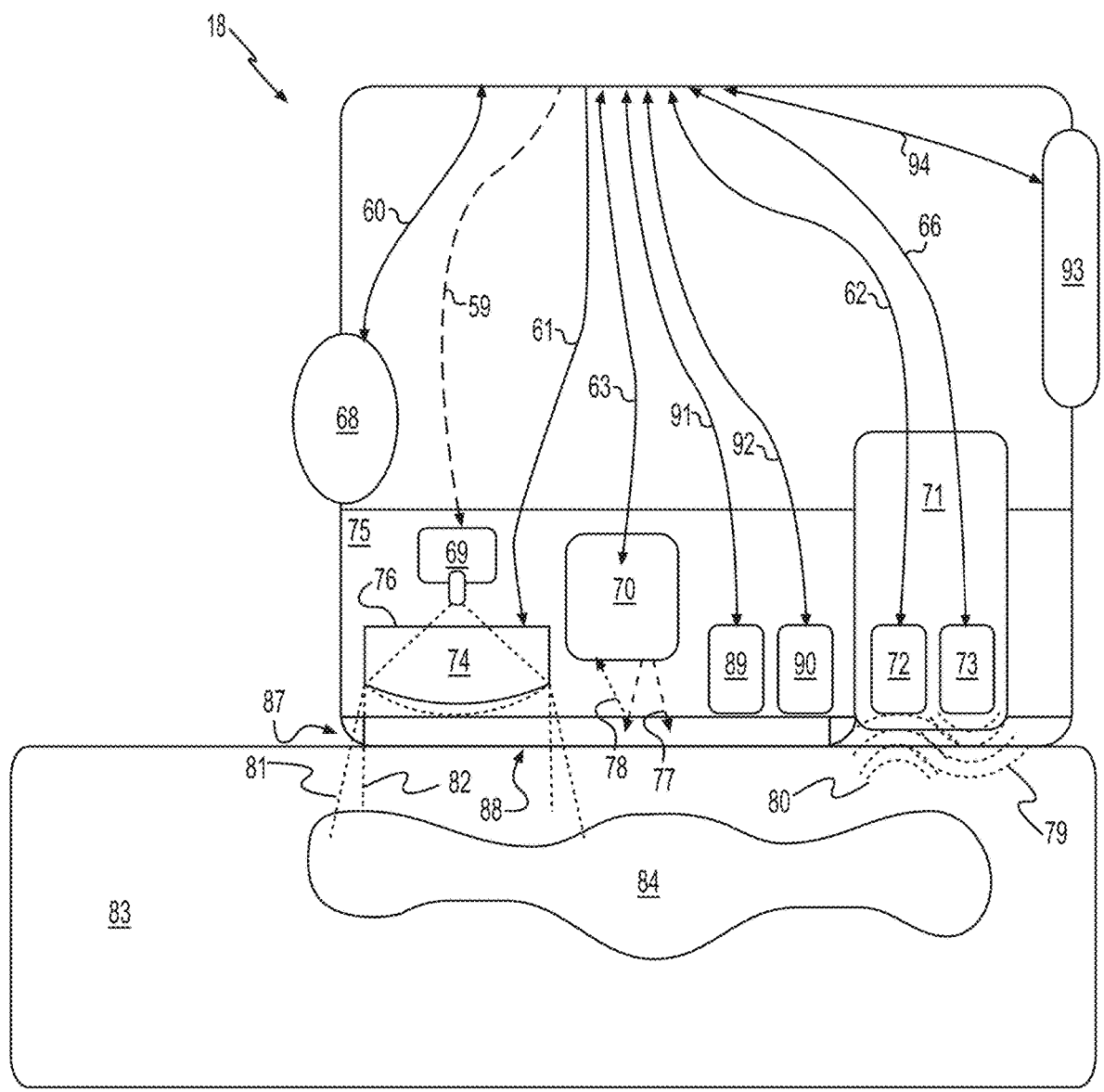
FIG. 3 is a schematic diagram of a therapy head of the disclosed phototherapy device according to one embodiment.

Referring now to FIG. 3, therapy head 18 may include an ultrasound transducer 71 having ultrasound transmitter 73 with its electrical leads 66, and ultrasound receiver 72 with its electrical leads 62. Therapy head 18 may further include RGB fiber optic sensor 70 with its electrical leads 63, electrically tuned optic lens 76 with its electrical leads 61, the distal end 69 of a fiber-optic cable 59 that carries the output light 74, a camera 89 with its electrical leads 91, and a proximity sensor 90 with its electrical leads 92. A finger switch 68 with its electrical leads 60 and electronic display 93 with its electrical leads 94 may also be included in therapy head 18. In some embodiments, an internal support 75 may serve to fix all components of therapy head 18 in place.

Electronic display 93 may optionally present the user with information regarding the treatment being provided to the patient. Such information may include, for example, the energy provided during the treatment session, a timer showing the length of the current treatment session, a power meter displaying the current output power levels, and/or an indicator communicating the relative focal length of the lens. Other information presented to the user on electronic display 93 may include real-time (average) power level(s), output light frequency or frequencies, and other data.

A bottom side of ultrasound transducer 71 may be substantially aligned with a lower surface of therapy head 18 such that when therapy head 18 is brought into contact with a patient's body 83, ultrasound transducer 71 contacts the skin of the patient 83. Gels or creams typically used for improving ultrasonic pulse transfer between an ultrasonic transducer and a patient's body would, in certain preferred embodiments, be applied to the patient's skin to facilitate transmission of ultrasound signals (e.g. 79, 80) and to minimize friction as therapy head 18 is moved over the skin of the patient 83. Outgoing ultrasound pulses 79 generated by ultrasound transmitter 73 may enter the patient and interact with patient's tissue (including internal structures 84). The resulting reflected ultrasound waves 80 may then be sensed by ultrasound receiver 72. If therapy head 18 is not in contact with the patient's body 83, the signal from ultrasound receiver 72 will typically be substantially reduced, indicating a non-contact therapy. Accordingly, ultrasound transducer 71 may serve to provide real-time morphologic information about the tissue directly beneath and around therapy head 18 as well as real-time detection of contact vs. non-contact therapy.

An optically transparent window 88 may also be included in some embodiments to separate the bottom of therapy head 18 from RGB fiber optic sensor 70 and electrically tuned optic lens 76. Optically transparent window 88 may optionally be sealed by O-ring 87. In some embodiments, optically transparent window 88 may serve to protect the optical instrumentation from contamination by any dirt or ultrasound gels that may be present (not specifically shown). To ensure proper functionality, RGB fiber optic sensor 70 may be positioned at least 1 cm from the bottom of therapy head 18 and window 88 to ensure the outgoing white light 77 achieves sufficient spot size so that the light reflected from the patient surface 78 has sufficient intensity and angle of incidence to be properly recorded. RGB fiber optic sensor 70 may serve to provide real-time morphologic information about the skin of the patient directly beneath therapy head 18. In some embodiments, it may be necessary to calibrate the RBG fiber optic sensor 70 to account for reflected light blocked by the optically transparent window 88.

In some embodiments, the bottom of the camera 89 and proximity sensor 90 may be in contact with the window 88 to minimize obstruction in the field of view. Camera 89 and proximity sensor 90 may serve to provide a digital photograph of the field of view as well as a measure of the distance between therapy head 18 and the patient's body 83. Combined, these two pieces of information may help provide an accurate scale of the field of view. The user may use touch-screen display 29 to trace the desired treatment area based on this scaled photograph of the patient. CPU 31 may then calculate the area of the users trace, and this accurate measurement of the treatment area may be used as guidance for the user during treatment as well as to potentially calculate the total treatment time prescribed.

In some circumstances, the output light 74 exiting the distal end 69 of fiber-optic cable 59 is inherently divergent. Accordingly, the output light 74 may, when necessary, be focused using a lens (e.g., electrically tuned optic lens 76). The electrically tuned optic lens 76 may be, in some embodiments, aligned less than 2 mm from the optically transparent window 88. Advantageously, the focal length of electrically tuned optic lens 76 may be adjusted using a control current that can change the curvature of lens 76 (in some embodiments, on the order of milliseconds), thereby changing the focal length of lens 76 in real-time. The position of optic lens 76 should therefore take into account this change in curvature to ensure there is enough room for the lens 76 to change shape without coming into direct contact with optically transparent window 88. The changing focal length of electrically tuned optic lens 76 may change the divergence of the output light beam 81 (wide) or 82 (narrow). This mechanism may also serve to appropriately focus the output light beam in real-time based on the feedback signals of, for example, the RGB fiber optic sensor 70 and ultrasound transducer 71. Electrically tuned optic lens 76 may include a shape changing polymer lens that is adjustable according to an applied current that may be provided by, for example, CPU 31. Control currents provided by the CPU 31 may be any acceptable control current range as required by the particular lens 74 (e.g., 0-500 mA or 0-250 mA, among others).

It will be recognized by those having skill in the art that a number of the components of the central control unit 19 may be housed within the therapy head 18 if desired. For example, light sources 48, 49, 50, 51 and/or their accompanying drivers 40, 41, 42, 43 may be housed in the therapy head in certain embodiments. The same may be true, for example, for CPU 31, power supply 23, or any other component. Further, certain other embodiments may combine the central control unit 19 and therapy head 18 into a single unit, rather than two components connected, for example, by a cable.

Figure 4:
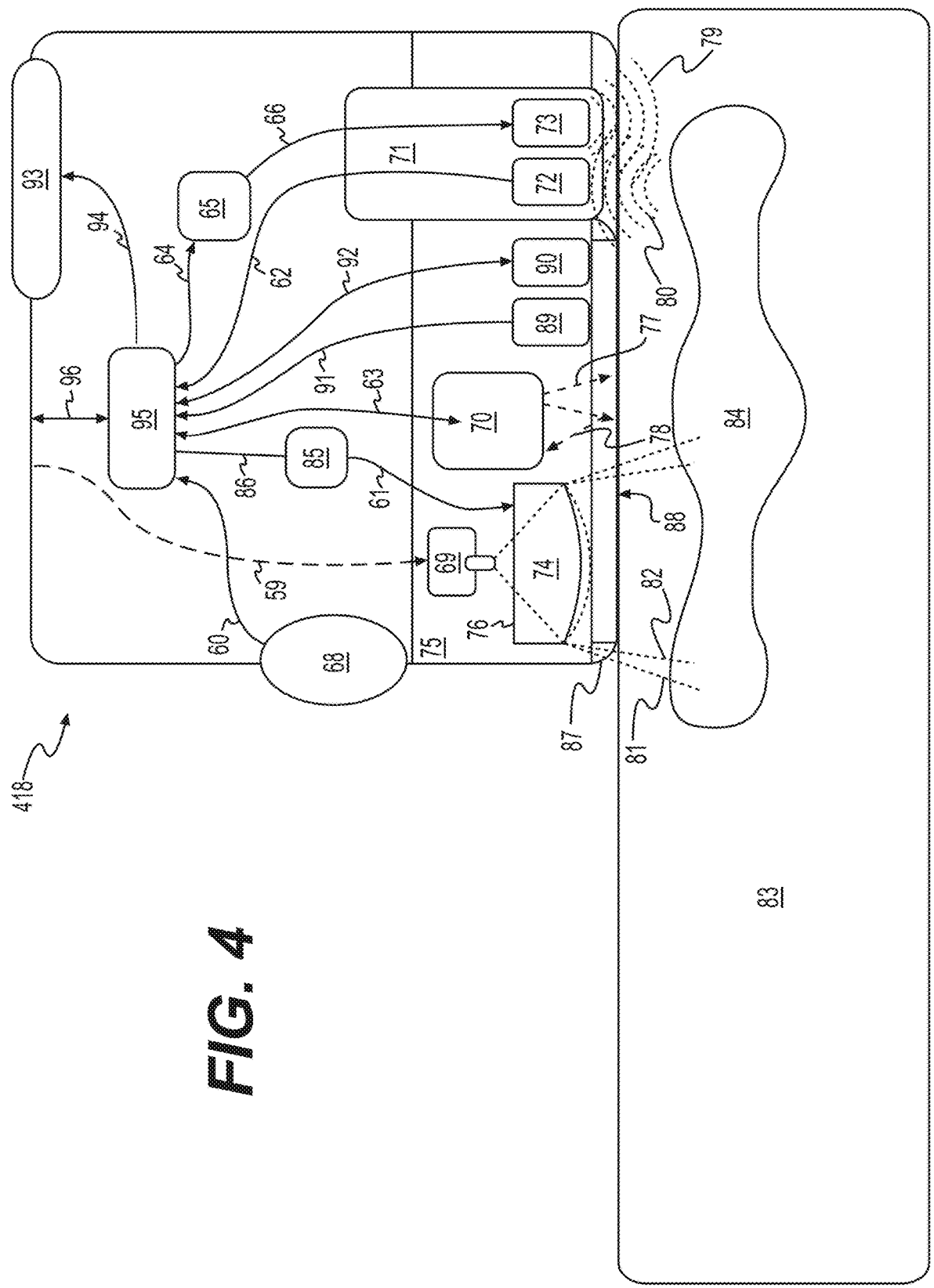
FIG. 4 is a schematic diagram of a therapy head of the disclosed phototherapy device according to another embodiment.
Figure 5:
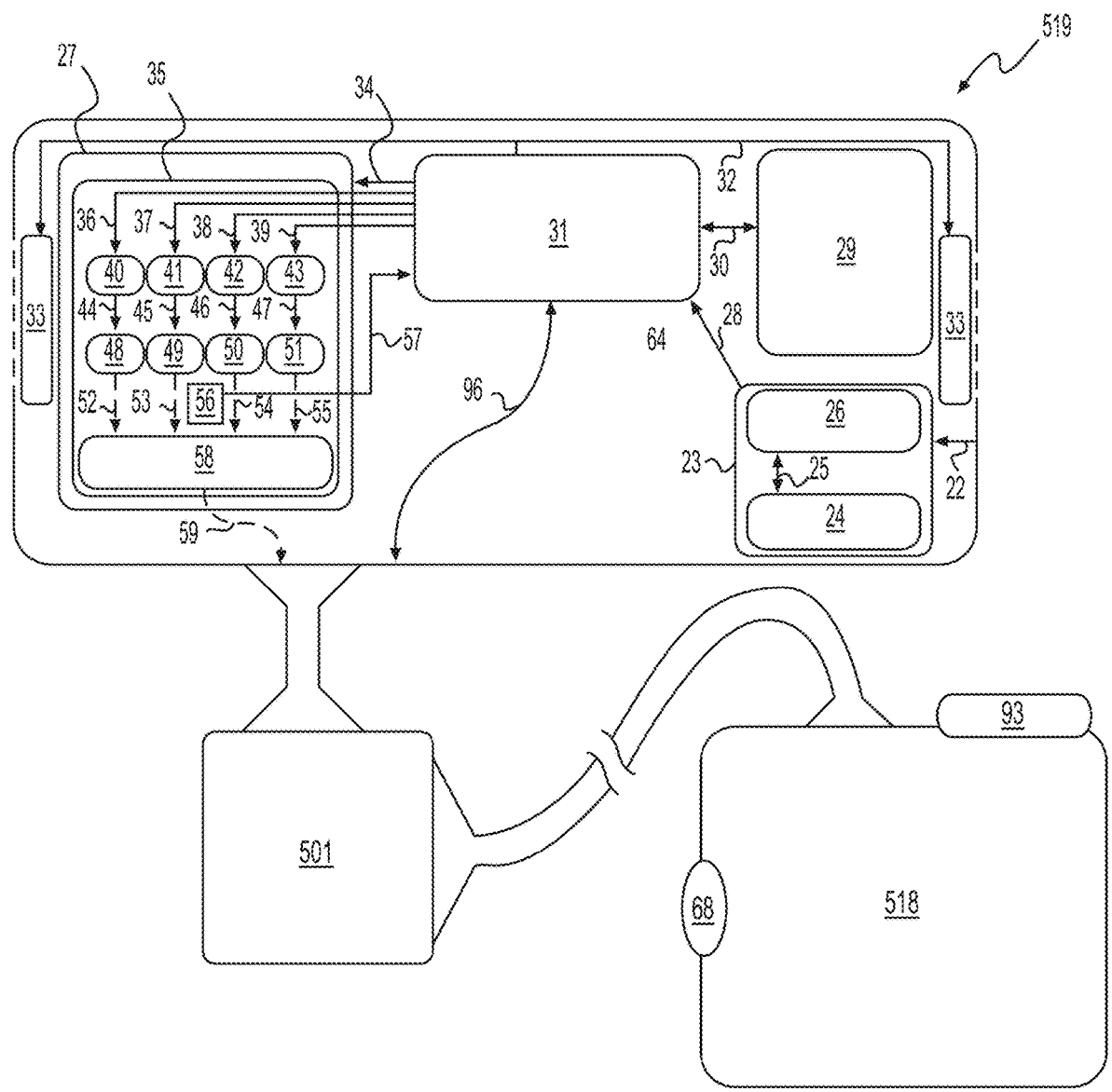
FIG. 5 is a schematic diagram of the disclosed phototherapy device according to another embodiment.

Referring now to FIG. 4, another exemplary embodiment of the present disclosure is presented that includes therapy head 418. Therapy head 418 may include, among other things, a second CPU 95 with its leads 96, driver 85 for electrically tuned optic lens 76, and an ultrasound generator 65 with its electrical leads 64. Accordingly, connections 60, 61, 86, 63, 91, 92, 62, 64, 66, or 94 may no longer travel through shielded cable 67 (or transmit via wireless connection or other means), but remain within therapy head 418, thereby reducing the number of signals required to travel between therapy head 418 and the central control unit (e.g., central control unit 519 (FIG. 5). As before, second CPU 95 may be coupled to other components within the device, including by way of one-way outgoing control, one-way incoming signals, and two-way feedback connections, among other power and/or electrical or optical communicative methods. Such embodiments may, for example, allow for use of an existing central control unit (e.g. central control unit 519) that may include light drivers 40, 41, 42, 43 and light sources 48, 49, 50, 51 (among other things), and add to such units additional functionality made possible by the components of therapy head 418, including for example ultrasound transducer 71, camera 89, proximity sensor 90, RGB fiber optic sensor 70, lens 76, and such associated hardware/software.

Referring now to FIG. 5, yet another alternative embodiment of the present disclosure is presented. In this exemplary embodiment, the device may be adapted to include a separate housing 501 that may be coupled and in operative communication with central control unit 519 and therapy head 518.

Figure 6B:
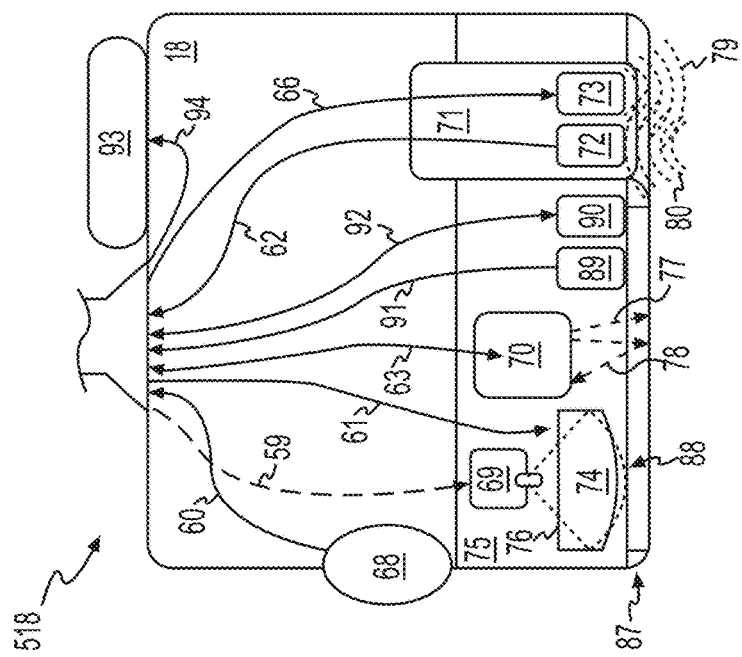
FIG. 6B is a schematic diagram of a therapy head of the disclosed phototherapy device according to another embodiment.
Figure 6A:
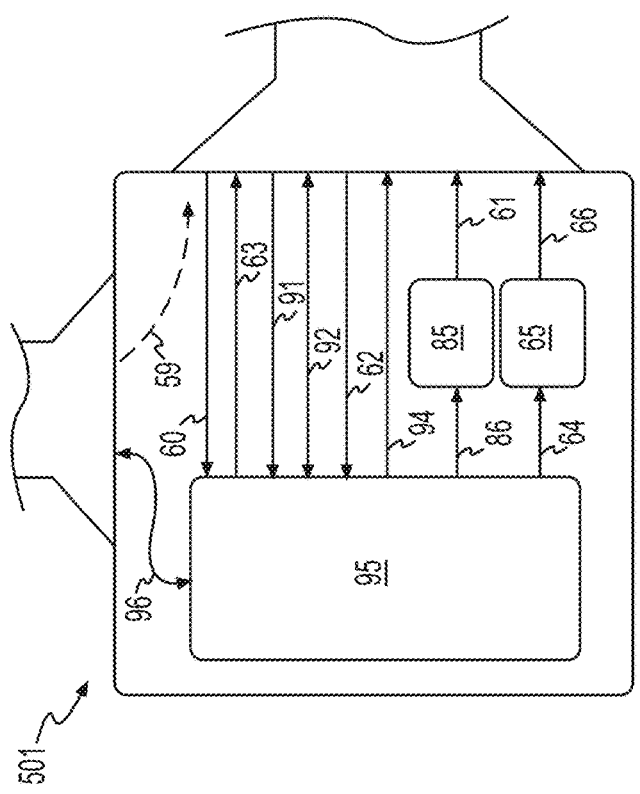
FIG. 6A is a schematic diagram of a CPU housing of the disclosed phototherapy device according to another embodiment.

As illustrated in FIGS. 6A and 6B, housing 501 may include the second CPU 95, driver 85, and ultrasound generator 65, along with connections 96, 60, 63, 91, 92, 62, 94, 86, 61, 64, and 66 to therapy head 518. Further, fiber optic waveguide 59 may pass through housing 501 from central control unit 519 to therapy head 518. Similar to the embodiment shown in FIG. 4, the device of FIG. 5 and FIGS. 6A and 6B may allow for use of an existing central control unit (e.g. unit 519). The housing 501 may provide for a reduction of hardware required within the therapy head 518, which may advantageously reduce the size and/or weight of therapy head 519, among other advantages.

Figure 7:
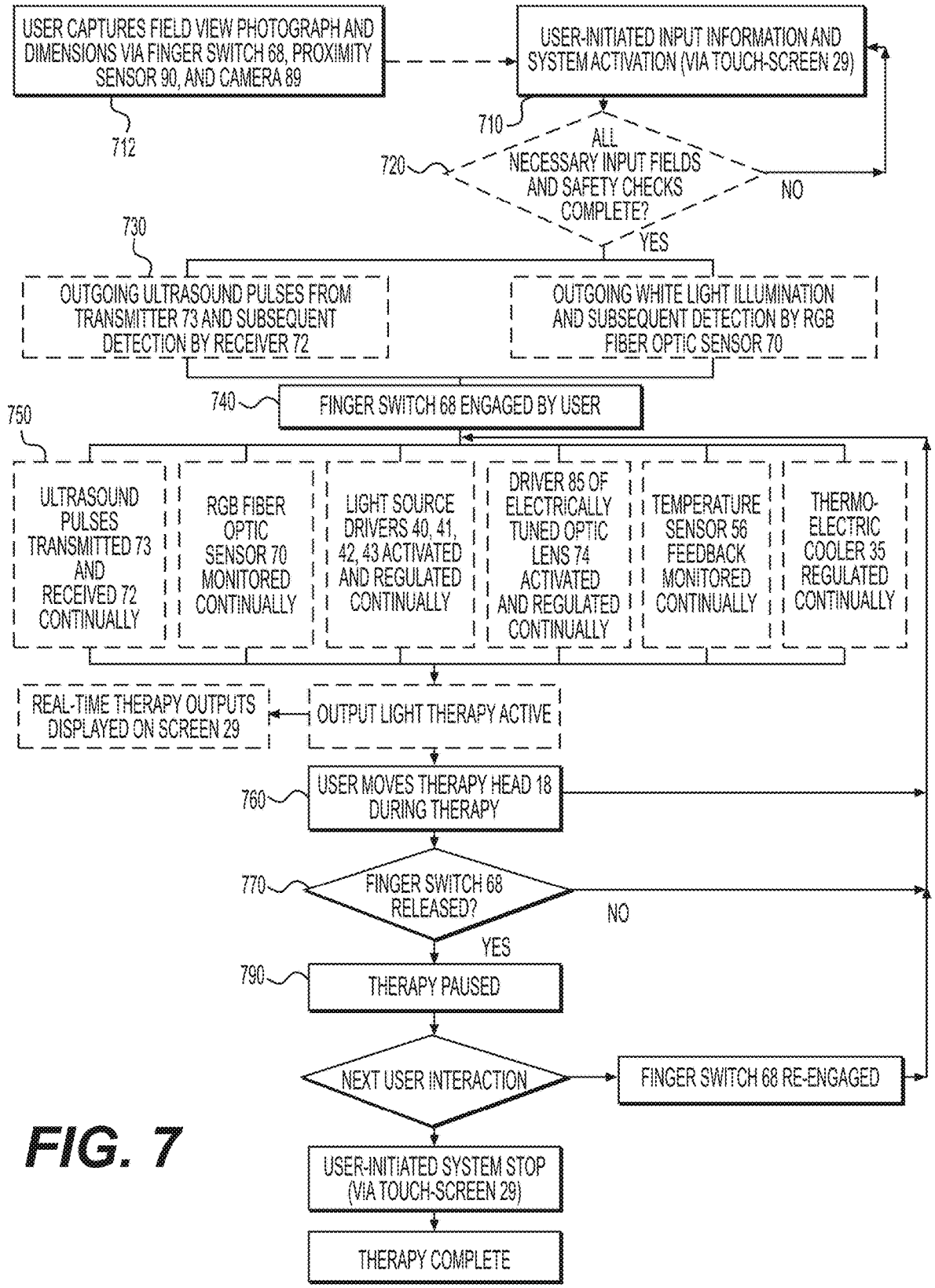
FIG. 7 is a flow chart illustrating an exemplary workflow of the methods disclosed herein according to one embodiment.

Referring now to FIG. 7, a workflow according to various embodiments of the present invention is presented. In such embodiments, at step 710, a user may interact with touch-screen display 29 via, for example, a graphical user interface (GUI). The user may enter certain preliminary information about the patient and his/her/its condition to be treated (for example, chronicity of the condition being treated (e.g., acute, chronic, etc.)), condition type (anti-inflammatory, analgesic, skeletal, superficial), and/or treatment duration. In various embodiments, one or more of these GUI inputs are used to determine certain initial output parameters for phototherapy (for example, light frequency/wavelength, average power, pulse shape/duration, etc.). In some embodiments, the GUI may also prompt the user to engage finger switch 68 at step 712 to initiate the camera 89 and/or proximity sensor 90, which may combine to take a scale-measured digital photograph of the treatment area. The user may then trace a desired treatment area on the picture, which can then be utilized by the system to calculate the to-scale area of the traced region as an additional input parameter.

In some embodiments, certain safeguards may be in place to ensure patient safety. At step 720, safeguards may be checked. Once one or more of the software's safeguards are checked and the system is enabled, the CPU 31 may send a signal to the ultrasound generator 65 to begin producing signals at step 730 and to generate outgoing white light illumination and/or detection by RGB fiber optic sensor 70. At step 740, a user may engage finger switch 68, which begins the real time monitoring and output light therapy shown at step 750, which includes activation of light source drivers 40, 41, 42, 43, driver 85 of electrically tuned optic lens 76. The monitoring also includes initiating the ultrasound transmitter 73 to produce outgoing ultrasound pulses 79 at regular time intervals. At a second set of regular time intervals, which in some embodiments are separated from the outgoing pulses by some fixed amount of time, ultrasound receiver 72 receives reflected ultrasound waves 80. The reflected ultrasound waves 80 may be reflected from the surface of the patient 83 and/or internal structures 84, and transmit information about the received waves back to the CPU 31. This information from ultrasound receiver 72 may then be used to determine certain morphologic properties about a patient's tissue beneath, adjacent to, and/or around the position of the therapy head 18. Similarly, CPU 31 may utilize input signals from the RGB fiber-optic sensor 70 and use that information to calculate further morphologic properties about a patient's tissue (e.g., below the position of the therapy head 18).

At step 760, the user moves therapy head 18 over the patient to provide the desired therapy, all while output characteristics are modified based on measured morphologic properties of the patient as dictated in step 750. This process repeats continuously until the finger switch is released (step 770), whereby the therapy is either paused or terminated by the user as shown in step 790. In some embodiments, finger switch 68 need not be depressed during the entirety of treatment, but may be, for example, depressed once to begin the treatment, and a second time to pause the treatment.

Using these morphologic properties of the patient that are being measured in real-time, CPU 31 may alter inputs to drivers 40, 41, 42, 43 of the light sources 48, 49, 50, 51 as well as to driver 85 of electrically tuned optic lens 76 to optimize treatment of the patient. Light sources 48, 49, 50, 51 produce light with intensity dictated by or proportional to the input signal from drivers 40, 41, 42, 43. In parallel to the production of light, CPU 31 may send a signal to driver 85 of electrically tuned optic lens 76 that changes the focal length of the lens, which in turn may change the shape of the beam 81, 82 of output light. Accordingly, therapeutic light output is modified in real-time based on real-time measurements of patient morphologic properties, thereby optimizing patient treatment.

Figure 8:
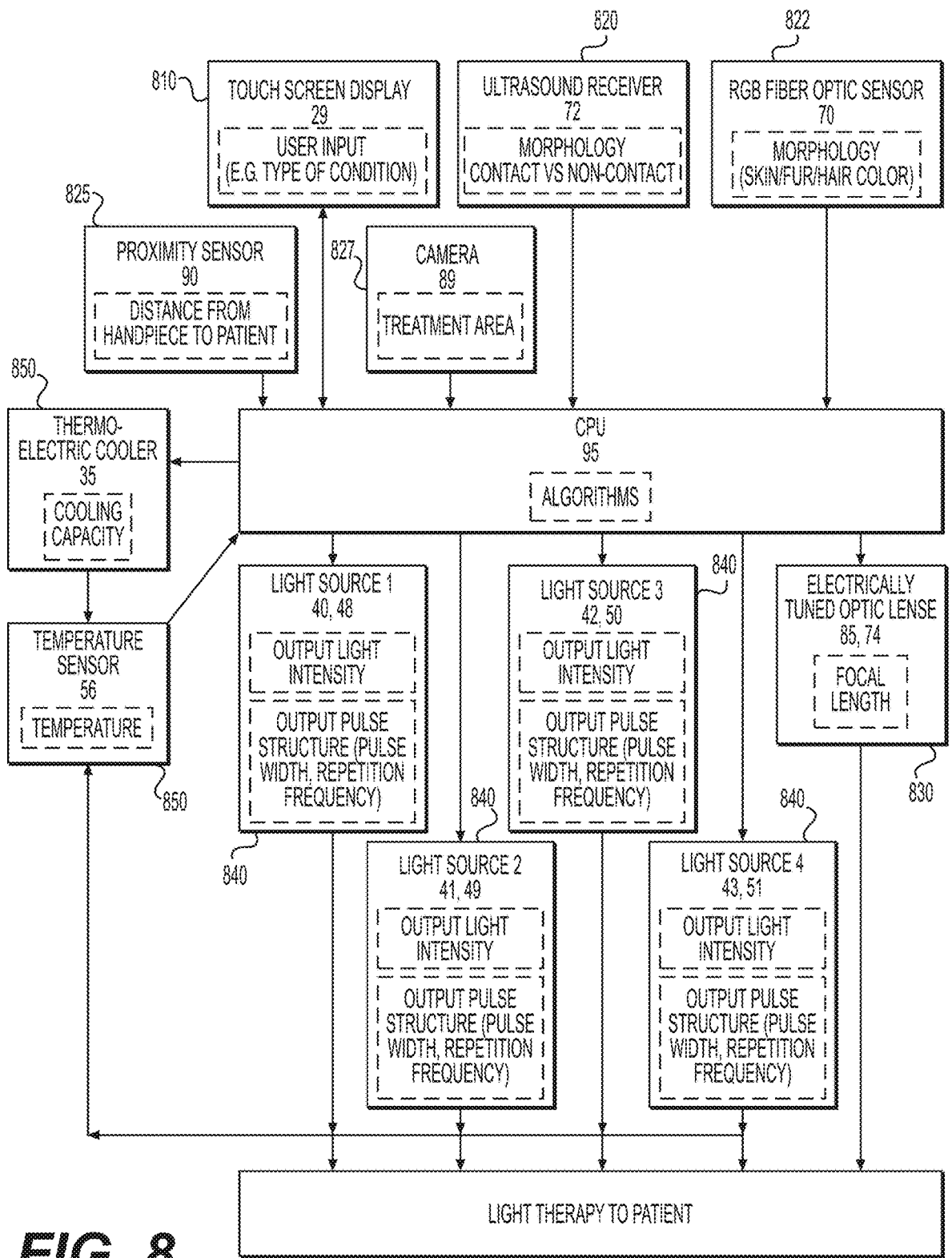
FIG. 8 is a block-diagram of an exemplary feedback circuit that may be used to determine output parameters of the disclosed phototherapy device according to one embodiment.

Referring now to FIG. 8, a block-diagram of an exemplary feedback circuit that may be used to determine output parameters of light therapy is presented. In some embodiments, CPU 31 may serve as a mediator of all inputs and outputs. The inputs may include user inputs 810 (e.g. information about the condition being treated) obtained via touch-screen display 29; real-time patient morphology data, including detection of contact vs. non-contact therapy 820 obtained via ultrasound receiver 72, real-time subcutaneous morphology data 822 obtained via ultrasound receiver 72, and/or real-time patient morphology data 822 (e.g., skin/fur/hair color) obtained via RGB fiber optic sensor 70. Inputs may also include treatment area 825 obtained via the combination of camera 89, user input via the GUI (e.g., touch screen 29), and data measuring the distance to the patient 827 obtained via proximity sensor 90. The outputs controlled by CPU 31 that may affect the light therapy delivered to the patient may include the focal length of the output light beam 830 controlled via driver 85 of electrically tuned optic lens 76, and the output light intensity and pulse structure 840 (e.g., pulse width and repetition frequency) of each light source 48, 49, 50, 51 controlled via independent drivers 40, 41, 42, 43. Also controlled in real-time may be the temperature of the internal components 850 by way of measuring temperature from temperature sensor 56 and controlling the cooling capacity of thermo-electric cooler 35 as well as the speed of the ventilation fans 33.

Figure 9:
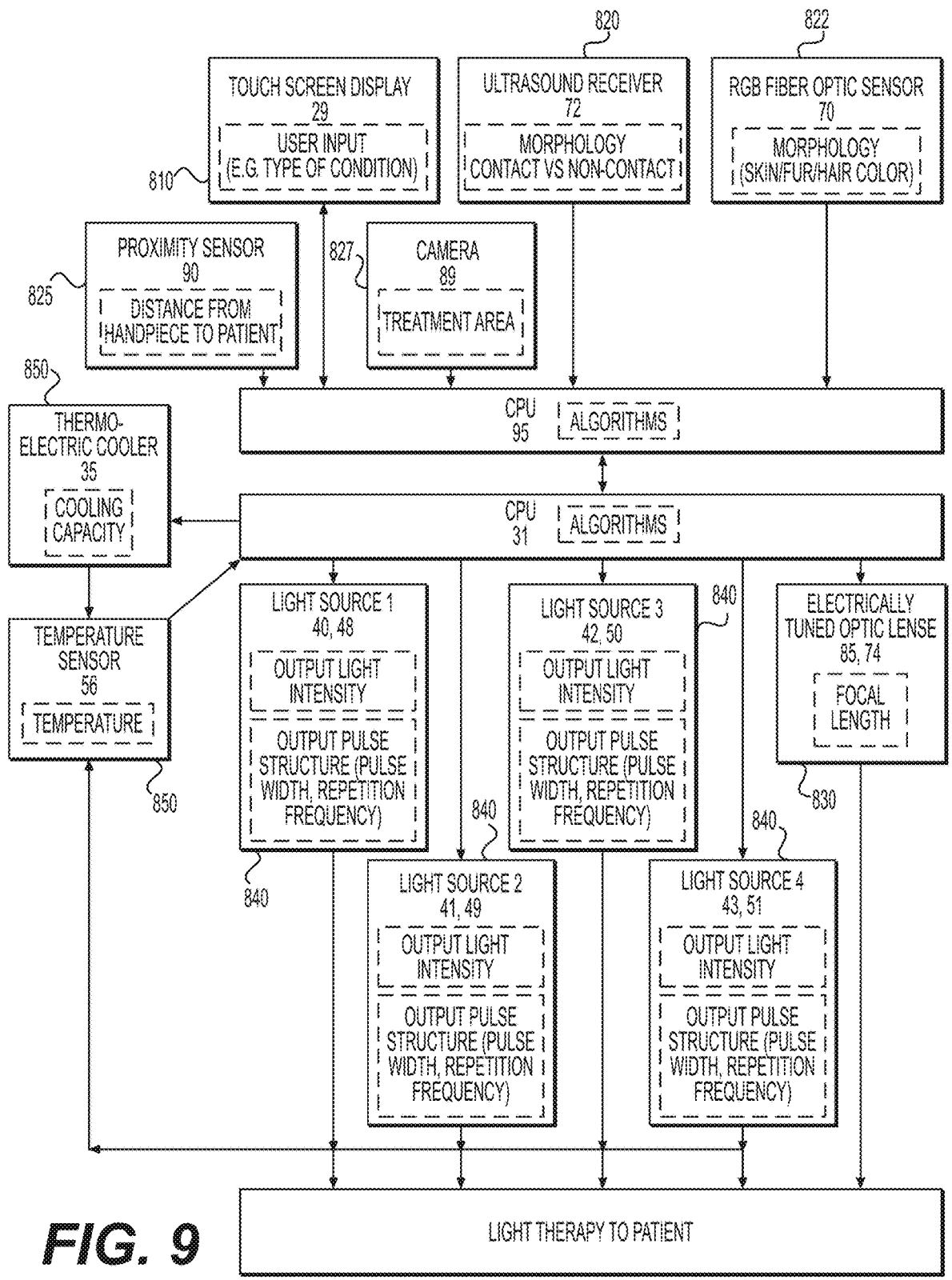
FIG. 9 is a block-diagram of another exemplary feedback circuit that may be used to determine output parameters of the disclosed phototherapy device according to one embodiment.

As previously disclosed, CPU 31 may include one or more separate CPU components, such as for example, CPU 95. An exemplary block diagram of a device including two CPUs (31 and 95) is included in FIG. 9. Persons having skill in the art will appreciate that the layouts disclosed herein are merely exemplary, and each component may be interconnected with each CPU and/or other components as desired.

Advantages of the phototherapy device in the present disclosure may include, without limitation, delivery of phototherapy that is individually tailored to the patient being treated, in real-time. Further, the protocol choice for treating patients may no longer be limited to broad estimations of very specific morphologic properties of the patient, all of which have been extensively shown to greatly impact the penetration of light and efficacy of therapy.

For the present disclosure, the terms "a," "an," and "the" refer to "one or more" when used herein, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items. As used herein, the term "and/or" includes any and all combinations of one or more of the associated listed items and may be abbreviated as "/".

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

It will be understood that when a feature or element is referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. The terminology used herein is for the purpose of describing particular embodiments only and is not intended to be limiting of the invention.

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations in use or operation in addition to the orientation depicted in the figures.

It will be understood that although the terms first and second are used herein to describe various features or elements, these features or elements should not be limited by these terms. These terms are only used to distinguish one feature or element from another feature or element. Thus, a first feature or element discussed below could be termed a second feature or element, and similarly, a second feature or element discussed below could be termed a first feature or element without departing from the teachings of the present invention.

Unless otherwise defined, all terms (including technical and scientific terms) and phrases used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

Although the foregoing subject matter has been described in some detail by way of illustration and example for purposes of clarity of understanding, it will be understood by those skilled in the art that certain changes and modifications can be practiced within the scope of the appended claims.

What is claimed is:

1. A phototherapy device comprising
a central processing unit;
a therapeutic light source of varying intensity output having a wavelength between 400-1100 nm;
at least one of a RGB sensor and an ultrasound generator and transducer, wherein the at least one of the RGB sensor and ultrasound generator and transducer provide information to the central processing unit for determining one or more morphologic properties of a patient; and
at least one of
a lens, wherein the lens comprises an electrically tuned optic lens having a focal length that can be manipulated by the central processing unit relative to the therapeutic light source output from the device, or
a touchscreen, a proximity sensor, and a camera, wherein the camera and the proximity sensor are configured to capture an image of an area to be treated and provide a scaled image to a user on the touchscreen;
wherein the central processing unit is configured to determine one or more morphologic properties of the patient and control output from the therapeutic light source in real-time based on the one or more morphologic properties.

2. The phototherapy device of claim 1, further comprising a temperature regulating mechanism.

3. The phototherapy device of claim 1, wherein the therapeutic light source comprises a plurality of light sources having discrete wavelengths and individually controllable intensities that are configured to be adjusted in real-time based on the one or more morphologic properties of the patient.

4. The phototherapy device of claim 1, wherein the therapeutic light source comprises one or more broad spectrum light sources having controllable spectrum and intensities.

5. A phototherapy device, comprising:
 a therapeutic light source of varying intensity output having a wavelength between 400-1100 nm;
 one or more of a RGB sensor and an ultrasound generator and transducer, wherein the one or more of the RGB sensor and ultrasound generator and transducer provide information to a first central processing unit for determining one or more morphologic properties of a patient;
 at least one of
  a lens, wherein the lens comprises an electrically tuned optic lens having a focal length that can be manipulated by the first central processing unit relative to the therapeutic light source output from the device, or
  a touchscreen, a proximity sensor, and a camera, wherein the camera and the proximity sensor are configured to capture an image of an area to be treated and provide a scaled image to a user on the touchscreen; and
 a second central processing unit operatively coupled to the first central processing unit, wherein the second central processing unit is configured to determine one or more morphologic properties of the patient and control output from the therapeutic light source in real-time based on the one or more morphologic properties.

6. The phototherapy device of claim 5, further comprising a therapy head and a CPU housing in operative communication, wherein the therapy head comprises the first central processing unit, output from the therapeutic light and the one or more of the RGB sensor and the ultrasound transducer, and the CPU housing comprises the second central processing unit.

7. The phototherapy device of claim 6, wherein the CPU housing further comprises the ultrasound generator.

8. A method of treating a patient using light therapy, the method comprising the steps of:
 a. providing a phototherapy device comprising a central processing unit and a therapeutic light source output having a wavelength between 400-1100 nm;
 b. inputting to the central processing unit at least one input;
 c. displaying treatment information to a user, wherein the treatment information comprises one or more of (a) energy provided during a treatment session; (b) a time associated with duration of the treatment session, (c) a power meter; and (d) a focal length indicator of a lens;
 d. delivering light therapy to the patient using a therapy head comprising the therapeutic light source output, based on any one or more of the at least one input;
 e. determining one or more morphological properties of the patient using one or more of:
  i. an ultrasound generator and transducer wherein ultrasound pulses are generated, the ultrasound generator and transducer being configured to transmit the ultrasound pulses to the patient via the ultrasound transducer, and measure, proximate to the ultrasound transducer, any ultrasound pulses reflected from the patient; and
  ii. a RGB sensor for sensing, at the RGB sensor, light information reflected from the patient;
 f. automatically adjusting properties of the therapeutic light source based on the one or more patient morphologic properties determined; and
 g. repeating steps b-f throughout a treatment period.

9. The method of claim 8, further comprising the step of providing a temperature regulating mechanism and a temperature sensor, wherein the temperature regulating mechanism is activated when the device reaches a predetermined temperature.

10. The method of claim 8, further comprising the steps of detecting in real-time whether the therapy head is in contact with the patient and one or more steps selected from the group comprising
 i) adjusting an intensity of the therapeutic light source,
 ii) adjusting the focal length of an electrically tunable lens, and
 iii) reducing the pulses of the ultrasound generator and transducer;
 when the therapy head is not in contact with the patient during treatment.

11. The method of claim 8, wherein the at least one input comprises any one of (a) chronicity of a condition being treated; (b) condition type, (c) treatment duration, and (d) an outline of a desired area to be treated.

12. The method of claim 11, wherein the at least one input is delivered via a touchscreen.

13. The method of claim 11, wherein the at least one input is delivered via a central control unit.

14. The method of claim 13, wherein the at least one input is delivered via the central control unit on a touchscreen display.

15. The method of claim 8, wherein the treatment information is displayed on the therapy head.

16. The method of claim 8 further comprising the steps of using a camera and a proximity sensor within the therapy head to acquire a to-scale image of a portion of the patient, inputting the limits of a desired treatment area, and calculating the treatment area based on this image and the limits of the desired treatment area.

\* \* \* \* \*